United States Patent
Backlund et al.

(10) Patent No.: US 6,783,622 B1
(45) Date of Patent: Aug. 31, 2004

(54) METHOD AND ARRANGEMENT FOR PRODUCING WEBS OF MATERIAL THAT HAVE DISCRETE PIECES OF MATERIAL MOUNTED THEREON

(75) Inventors: Lennart Backlund, Skene (SE); Terje Skog, Nykirke (NO)

(73) Assignee: SCA Hygiene Products AB, Göteborg (SE)

(*) Notice: Subject to any disclaimer, the term of this patent is extended or adjusted under 35 U.S.C. 154(b) by 0 days.

(21) Appl. No.: 09/979,075

(22) PCT Filed: May 10, 2000

(86) PCT No.: PCT/SE00/00927

§ 371 (c)(1),
(2), (4) Date: Jan. 18, 2002

(87) PCT Pub. No.: WO00/73031

PCT Pub. Date: Dec. 7, 2000

(30) Foreign Application Priority Data

May 18, 1999 (SE) .............................................. 9901800

(51) Int. Cl.[7] ........................ B32B 31/00; B32B 31/18; B32B 31/20; B32B 31/10
(52) U.S. Cl. ....................... 156/250; 156/265; 156/269; 156/272.2
(58) Field of Search ................................ 156/250, 253, 156/256, 257, 265, 269, 272.2, 349, 494, 510, 517, 519, 583, 583.1, 566

(56) References Cited

U.S. PATENT DOCUMENTS

| | | | | |
|---|---|---|---|---|
| 4,360,398 A | * | 11/1982 | Sabee ........................... | 156/164 |
| 4,364,787 A | * | 12/1982 | Radzins ........................ | 156/164 |
| 4,397,704 A | * | 8/1983 | Frick ............................ | 156/201 |
| 4,795,510 A | * | 1/1989 | Wittrock et al. ............... | 156/64 |
| 4,822,437 A | * | 4/1989 | Bryniarski et al. ........... | 156/252 |
| 4,838,964 A | * | 6/1989 | Thomsen et al. ............. | 156/73.1 |
| 5,021,111 A | * | 6/1991 | Swenson ...................... | 156/264 |
| 5,286,543 A | * | 2/1994 | Ungpiyakul et al. ....... | 428/32.24 |
| 5,407,513 A | * | 4/1995 | Hayden et al. .............. | 156/265 |
| 5,643,396 A | | 7/1997 | Rajala et al. | |

FOREIGN PATENT DOCUMENTS

| | | |
|---|---|---|
| EP | 358382 | 3/1990 |
| JP | 8052696 | 2/1996 |
| WO | 98/41401 | 9/1998 |
| WO | WO 98/41401 * 9/1998 | ........... B32B/31/00 |

* cited by examiner

Primary Examiner—J. A. Lorengo
(74) Attorney, Agent, or Firm—Burns Doane Swecker & Mathis LLP

(57) ABSTRACT

A method of producing material in the form of a material web (4) that has discrete pieces of material (6) mounted thereon without the using of an adhesive agent and while using only one single anvil roll, and an arrangement (10) for carrying out the method and comprising an anvil roll (2) which rotates about its longitudinal axis and which is intended to be partially embraced by or be tangential to said web (4), said roll (2) carrying sequentially as seen in its direction of rotation at least one cutting means (1) for cutting discrete pieces from a material (6), and a bonding or fastening (5), such as ultrasound welding means, wherein the anvil roll (2) forms a counterpressure means for a coaction with the cutting means (1) and the bonding means (5), wherein said roll includes said holding means (7) for holding the cut discrete pieces of material (6) against the roll (2) prior to bonding or fastening said discrete pieces to said web by means of said bonding means (5).

22 Claims, 1 Drawing Sheet

Figure 1:
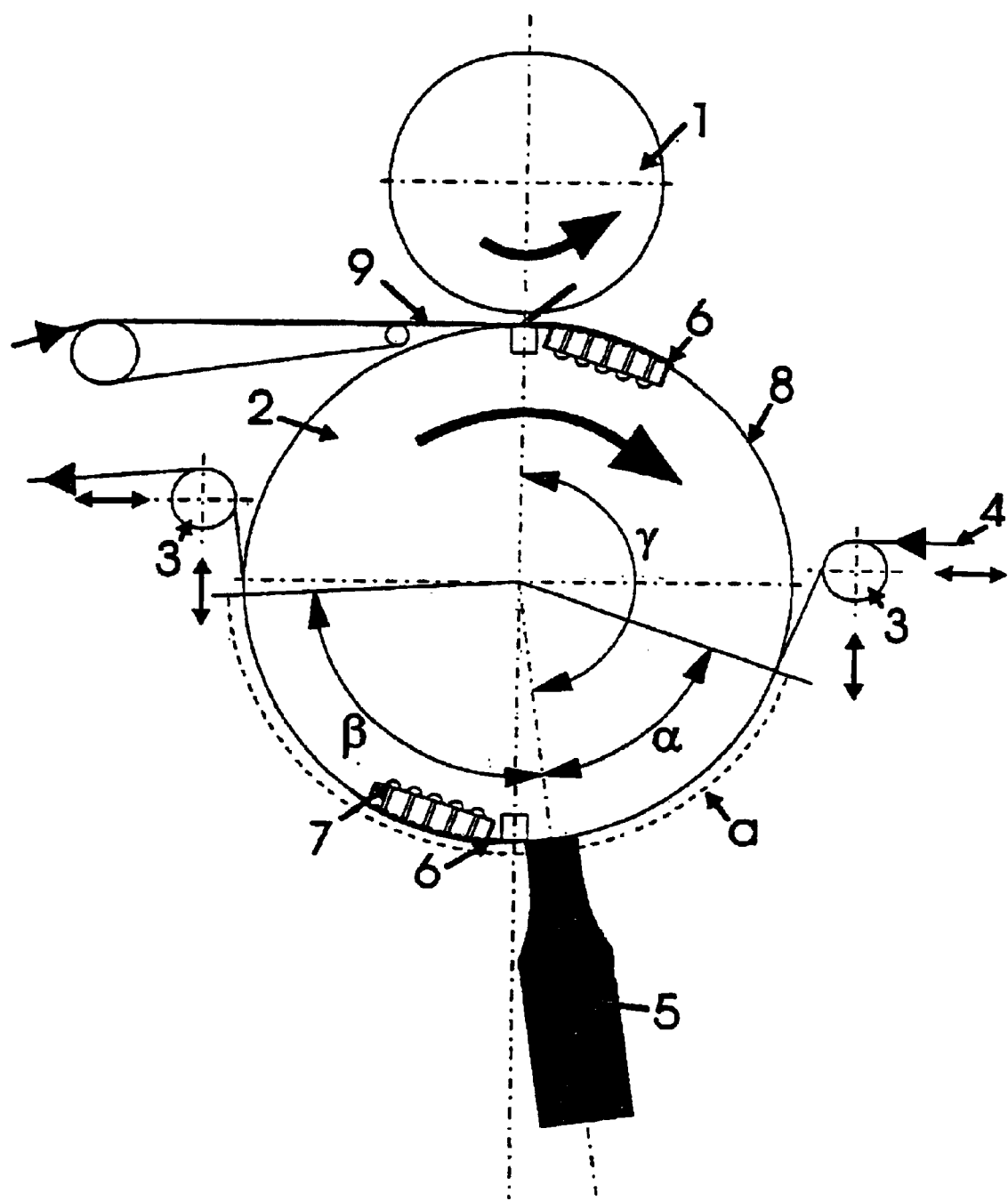

METHOD AND ARRANGEMENT FOR PRODUCING WEBS OF MATERIAL THAT HAVE DISCRETE PIECES OF MATERIAL MOUNTED THEREON

FIELD OF INVENTION

The present invention relates to a method of producing webs of material that have discrete pieces of material mounted thereon. The invention also relates to an arrangement for carrying out the method.

BACKGROUND OF THE INVENTION

The manufacture of certain sheets of material that are intended for the production of absorbent articles for instance, such as diapers, sanitary napkins, incontinence protectors, panty liners and like articles, sometimes comprises mounting and bonding discrete pieces of material on and to travelling webs of material. These discrete pieces are normally glued to the web, although they may alternatively be welded, there being required several so-called anvil rolls against which the travelling web is pressed and passes tangentially thereto or is partially embraced by one of the anvil rolls carrying said pieces of material, wherewith said pieces are brought into contact with the travelling web by means of said anvil roll.

The transfer of cut pieces of material from the anvil roll to the travelling web is often facilitated with the aid of glue or some other adhesive agent In this regard, the cut pieces of material are adhered to the anvil roll and then transferred to the travelling web as said web lies against the anvil roll, by virtue of rotation of said roll. The use of glue in this process increases the "stop time" and therewith lowers productivity and also increases material consumption, which has a negative affect on the price of the product, among other things.

JP-A-8052696 describes a cutting unit for cutting sanitary articles from a roll of material. The cutting unit includes an anvil roll and a cutting roller which are arranged opposite one another. The sanitary articles cut from the reel of material are sucked firmly to the surface of the cutting roller and transferred to a feed roll.

One problem associated with the use of the same anvil roll for cutting (clipping), transferring and bonding the pieces of material to the web is that an adhesive agent, such as glue, is required to this end. If the pieces of material are to be welded to the web for instance, it is necessary in the case of present technology to hold the loose pieces of material firmly during different transfer occasions between several anvil rolls. This requires the provision of more equipment and impairs the accuracy in which the pieces of material are applied to the web, resulting in poorer product quality.

It is thus desirable to be able to utilise one and the same anvil roll for all phases without needing to use glue or any other adhesive agent.

SUMMARY OF THE INVENTION

The object of the invention is to solve the aforesaid problems. This object is achieved in accordance with the invention with a method and with an arrangement for producing webs of material that have pieces of material mounted thereon, said method and arrangement comprising the use of one single anvil roll which cuts, accelerates, transfers and joins the discrete pieces of material to the travelling web in the absence of glue or any other adhesive agent The pieces are mounted on the web by virtue of the anvil roll comprising means for holding said pieces against the anvil roll subsequent to cutting out said pieces, for transferring said pieces to the travelling web and for fastening said pieces thereto.

According to one preferred embodiment of the invention, the method comprises the steps of:

cutting discrete pieces from at least one material with the aid of cutting means, preferably in the form of a rotating cutter roll while using the anvil roll as a counterpressure means;

firmly holding and applying said discrete pieces onto at least one web of material that moves against the anvil roll, by using the anvil roll as a transfer element;

fastening said discrete pieces to said at least one travelling web with the aid of fastener means, wherein said pieces are mutually separated by cutting, accelerated whilst firmly held and then fastened or bonded to said at least one web of material, without the use of adhesive agent, through the medium of one and the same anvil roll and by means of said fastening means whilst using the anvil roll as a counterpressure, means even when fastening said discrete pieces to said web, and wherewith the discrete pieces are held firmly by means of holding means provided on the anvil roll, said pieces and said web running together against the anvil roll before and after bonding of said pieces to said web.

According to another preferred embodiment of the invention, the arrangement for carrying out the method includes an anvil roll which is rotatable about its longitudinal axis and which is partly embraced by or tangential to said at least one web of material and which carries sequentially in its direction of rotation means for cutting discrete pieces from at least one material, and means for fastening or bonding said discrete pieces to said web, wherein the anvil roll includes between said cutting means and said fastening means further means which function to hold the discrete pieces of material against the roll prior to fastening said pieces to said web with the aid of said fastening means.

The pieces of material are preferably held to the anvil roll by suction, wherewith the means for holding said pieces may, for instance, comprise vacuum generating means, means that utilise static electricity or a mechanically working device.

The pieces are preferably fastened to the web by welding, such as ultrasound welding, or by some other type of heat-applying method and/or device, such as a hot roll, laser, thermobonding device, etc.

A significant advantage afforded by the inventive method and the inventive arrangement resides in the simplification that is achieved with the use of solely one single anvil roll for all of the steps involving cutting, accelerating, and transferring pieces of material to the travelling web of material and fastening said pieces to said web. A farther advantage is that it is not necessary to use glue or some other adhesive agent to fasten said pieces to the web. Furthermore, since the pieces of material and the web runs together against the anvil roll before and after bonding it is easy to control and synchronise the feeding thereof to the bonding device and allow ample time for cooling of the bonds.

DETAILED DESCRIPTION OF THE INVENTION

The invention will now be described in more detail with reference to the accompanying drawing, in which FIG. 1 illustrates schematically one embodiment of an inventive arrangement.

DETAILED DESCRIPTION OF THE INVENTION

The invention shall not be considered to be limited to the embodiment described below, as a number of further modifications are conceivable within the scope of the accompanying claims.

The arrangement 10 shown in FIG. 1 comprises a cutting roller 1, an anvil roll 2, and associated guide rollers 3. A web of material 4 onto which pieces of material shall be mounted moves in abutment with the anvil roll 2 in the arrowed direction, with an infeed angle $\alpha$ and a relief angle $\beta$. The size of the surface a with which the web 4 is in abutment with the anvil roll 2 and the angles $\alpha$, $\beta$ are adjusted by commensurate adjustment of the two guide rollers 3 in a vertical or a horizontal direction, as illustrated with the double-headed arrows.

As the web 4 lies against the anvil roll 2, welding energy is applied, appropriately with a welding device 5, so as to fasten or bond the pieces 6 to the travelling web 4. The welding device 5 may comprise an ultrasound welding device that includes a horn. When welding, it is suitable to use positional control of the horn so as to maintain the correct distance between welding horn and anvil pattern. Alternatively, any other appropriate type of heat applying device can be used instead of a welding device, such as a heating roll, laser or like device.

The web 4 is relieved from the anvil roll 2 at a relief angle $\beta$, such that the web 4 will have time to cool down (if necessary) subsequent to bonding the pieces of material thereto and prior to pulling the web 4 from the anvil roll 2. After said bonding process, the cooling temperature and cooling time must be adapted with respect to the quantities of material used and also with respect to the materials from which the web 4 and said pieces 6 are comprised.

The discrete pieces of material may comprise wadding, adhesive tape, etc.

The web may consist of polypropylene, polyethylene, etc.

The relief angle $\beta$ can be varied to provide different cooling times subsequent to bonding or fastening the discrete pieces to the web.

When using an anvil roll that has two holding devices, as in the case of FIG. 1, the relief angle $\beta$ may suitably vary between 0 and 270°. Other angles apply with other numbers of holding devices. Although not shown, it is also possible to cool subsequent to applying said discrete pieces, suitably with the aid of some form of cooling device.

The material 9 from which said discrete pieces 6 are formed is fed in between the cutter roll 1 and the anvil roll 2, wherewith the cutter roll 1 cuts the material into appropriate discrete pieces 6 against the anvil roll 2, said pieces being held firmly to the anvil roll 2 by holding means 7, such as vacuum means or the like. The cut pieces 6 are transported on the barrel surface 8 of said anvil roll 2 as said roll rotates about its longitudinal axis at a constant or varying speed, which is clockwise in the case of the embodiment illustrated in FIG. 1.

The pieces are suitably cut at a relief angle $\beta$ of 0°, normally vertical above the fastening point.

Web speeds, fastening times, such as weld times, and rotational speeds will depend on material qualities, weights per unit area, fastening methods, e.g. different welding patterns, weld gap and the number of cutters (knives) on the cutting roll.

It is essential that the bond that joins the discrete pieces 6 to the travelling web 4 is strong enough to resist the force occurring when the web 4 is relieved from the anvil roll 2.

It has also been found that the contact angle $\alpha$ between the anvil roll 2 and the travelling web 4 can be varied. This can influence the infeed of the travelling web into the gap or nip between the anvil roll and the bonding device, and can also influence the accuracy with which the discrete pieces 6 are applied. For instance, when using an anvil roll that has two holding device, as in FIG. 1, and said pieces are welded to the web, the contact angle $\alpha$ will preferably be between 0 and 160°. Other angles apply in the case of different numbers of holding devices.

When using an anvil roll that has two holding devices, as in FIG. 1, the angle $\gamma$ between the cutting roll and the bonding device will preferably be between 90 and 180°. However, this angle will depend on the distance between cutting point and bonding point, e.g. welding point, so that the bond is not affected by vibrations from the cutting roll. Other angles apply with different members of holding devices.

What is claimed is:

1. A method of producing material in the form of a material web that has mounted thereon discrete pieces of material intended for use in the manufacture of absorbent articles, said method comprising the steps of:

cutting discrete pieces from at least one material with the aid of a cutter while using an anvil roll as a counterpressure roll;

firmly holding the discrete pieces cut by the cutter on the anvil roll so as to transfer said discrete pieces onto at least one web of material that is guided into contact with the anvil roll;

bonding the discrete pieces of material to said at least one travelling web while being in contact with the anvil roll with the aid of bonding means, and guiding the at least one web of material into contact with the anvil roll along a portion of the circumference of the anvil roll so that said discrete places and said web are running together against the anvil roll before and after bonding of said pieces to said web, the holding and the bonding being made in the absence of any adhesion agent, wherewith the discrete pieces are held firmly by means of holding devices provided on the anvil roll.

2. A method according to claim 1, characterised by holding said discrete pieces with th aid of a vacuum.

3. A method according to claim 1, characterised by holding said discrete pieces by means of static electricity.

4. A method according to claim 1, characterised by holding the discrete pieces mechanically.

5. A method according to claim 1, characterised by heatbonding said discrete pieces.

6. A method according to claim 5, characterised wherein by weld-bonding said discrete pieces.

7. A method according to claim 5, characterized by bonding said pieces with the aid of a heat delivering device.

8. An arrangement for bonding or joining discrete pieces of material to material in the form of at least one travelling web, intended for use in the manufacture of absorbent articles, said arrangement comprising an anvil roll which rotates about its longitudinal axis and forms a counterpressure means of a cutting means for cutting discrete pieces from at least one material and of a bonding means or fastening means, the cutter and the remaining parts of the bonding means being located at different locations around the periphery of the anvil roll, the cutter being placed first as seen in the direction of rotation of the anvil roll, wherein the anvil roll includes holding means for holding said discrete pieces to said web with the aid of said bonding means, and the arrangement includes means for holding the web In abutment with the anvil roll before and after passage of the bonding means.

9. An arrangement according to claim 8, wherein the holding means is a vacuum suction means.

10. An arrangement according to claim 8, wherein the holding means utilizes static electricity.

11. An arrangement according to claim 8, wherein the holding means is a mechanical device.

12. An arrangement according to claim 8, wherein the bonding device is a welding device.

13. An arrangement according to claim 8, wherein the bonding device is a hot roll.

14. An arrangement according to claim 8, wherein the cutting roll and the bonding means are disposed essentially in fine with each other on opposite sides of the anvil roll, wherein an angle γ between cutting points and welding points ≈180°.

15. An arrangement according to claim 8, characterised by guide rollers which are adapted to vary the size of an abutment surface a, wherewith said at least one material web abuts the anvil roll, and in that the guide rolls can be adjusted vertically and laterally.

16. A method according to claim 1, wherein the absorbent articles are diapers, pants-type diapers, sanitary napkins, and incontinence protectors.

17. A method a according to claim 5, characterized by ultrasound welding said pieces.

18. A method according to claim 7, wherein the heat delivering device is a heating roll.

19. An arrangement according to claim 8, wherein the absorbent articles are diapers, pants-type diapers, sanitary napkins, and incontinence protectors.

20. An arrangement according to claim 12, wherein the welding device is an ultrasound welding device.

21. An arrangement according to claim 11, wherein the mechanical device is an edge that projects out radially from the anvil roll.

22. A method according to claim 1, wherein the cutter is in the form of a rotary cutter roll.

* * * * *